United States Patent [19]
Andresen et al.

[11] Patent Number: 5,124,653
[45] Date of Patent: Jun. 23, 1992

[54] METHOD AND APPARATUS FOR DETERMINING THE CONCENTRATION OF COMPOUNDS IN A GAS MIXTURE BY MICROWAVE GAS ANALYSIS

[76] Inventors: Uwe Andresen, Eiderstedter Strasse 17, 2352 Bordesholm; Helmut Dreizler, Klausdorfer Strasse 139, 2300 Kiel-Altenholz; Christof Keussen, Knorrstrasse 16; Wolfgang Stahl, Boninstrasse 31, both of 2300 Kiel, all of Fed. Rep. of Germany

[21] Appl. No.: 573,781

[22] Filed: Aug. 28, 1990

[30] Foreign Application Priority Data

Sep. 1, 1989 [DE] Fed. Rep. of Germany ....... 3929079

[51] Int. Cl.[5] ............................................. G01N 22/00
[52] U.S. Cl. .................................. 324/636; 324/633; 73/23.37
[58] Field of Search ............... 324/632, 633, 636, 629; 73/23.22, 23.35–23.37, 23.4, 23.42; 356/316

[56] References Cited

U.S. PATENT DOCUMENTS

| | | | |
|---|---|---|---|
| 2,882,493 | 4/1959 | Dicke | 324/636 X |
| 4,050,015 | 9/1977 | Zöllner | 324/636 |
| 4,110,686 | 8/1978 | Leskovar et al. | 324/636 |
| 4,369,404 | 1/1983 | Flygare et al. | 324/636 |

Primary Examiner—Jack B. Harvey

[57] ABSTRACT

In a method and apparatus for the analysis of gaseous compounds, especially for determining the concentration of a gas in a gas mixture by microwave spectroscopy, pulsed microwave radiation is coupled into a resonator which is tunable to various frequencies and which is disposed in an evacuated receiver. Either air or any gas mixture including the compounds to be determined is admitted to the receiver as a pulsed molecular jet. As a result of the microwave pulse the gas compound to be determined generates an emission which is coupled out from the resonator during the intervals between the incident microwave pulses. After adjusting by mixing to frequencies in a range of preferably below 50 MHz the measured signal is digitized and analyzed possibly by Fourier analysis.

20 Claims, 1 Drawing Sheet

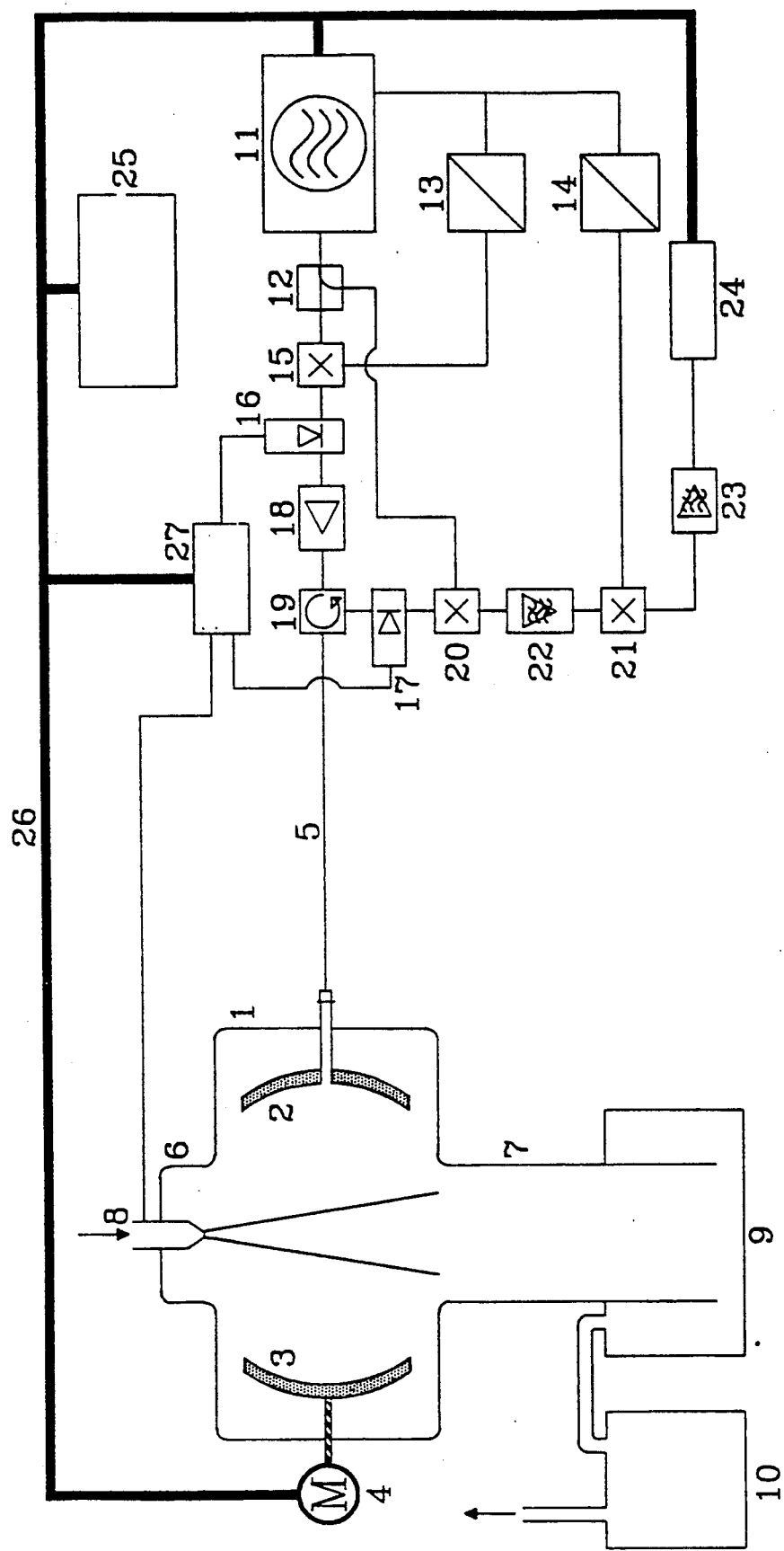

METHOD AND APPARATUS FOR DETERMINING THE CONCENTRATION OF COMPOUNDS IN A GAS MIXTURE BY MICROWAVE GAS ANALYSIS

BACKGROUND OF THE INVENTION

The invention relates to a method for identifying gaseous compounds and determining their concentration in a gas mixture by analysis of an emission spectrum generated by rotational transitions of molecules in gaseous substances exposed to microwave irradiation and to an apparatus for performing the method.

It is known that the composition of gas mixtures, but also of liquids and solids which can be converted to gaseous states in a suitable manner, can be quantitatively determined by microwave irradiation. Irradiation of gases by microwaves of a suitably selected frequency stimulates the molecules of a respective one of the gases in the gas mixture to be analyzed to undergo rotational transitions which are typical for the molecule such that knowledge of the rotation frequencies of various gases permits their identification in the gas mixture.

In a method and apparatus disclosed in DE-OS 3622957, the absorption of frequencies from the incident microwave radiation is utilized for analysis purposes. Herein the absorption lines are split by application of an electric field resulting in the "Stark" effect which provides for a relatively good analysis sensitivity because of the Stark effect modulation. It is also known that the width of the absorption lines can be reduced and consequently the resolution of the measuring method can be improved if the analysis is performed in a space maintained at reduced pressure.

In this method it is considered to be disadvantageous that, for performing the analysis, which is also called "Stark-spectroscopy", it is generally necessary that the molecules of the gas to be analyzed have electric dipole moments of a strength of at least 0.2 Debye. Also the quantitative determinations depend greatly on the pressure and temperature in the measuring space which therefore need to be exactly determined and controlled but still they may be sources for incorrect measuring results.

The magazine "Review of Scientific Instruments", Vol. 52, No. 1, 1981, pages 33–45 discloses a measuring method, similar to the one with which the present invention is concerned, for investigating the resonance transitions of short-lived molecule structures. The apparatus utilized in this method is a microwave spectrometer in which the particles of a gas added to an inert carrier gas under approximately atmospheric pressure are admitted to an evacuated receiver by way of a preferably pulsed admission valve and are conducted through a microwave field which is generated in a Fabry-Perot resonator. Since the expansion of the gases in the receiver is an adiabatic process, the gas temperature is lowered which facilitates the investigation, by means of microwave irradiation, of molecules which are added to a gas used as a carrier gas. The rotation lines of low rotational quantum numbers to be observed are intensified and complicated rotation spectra with a large number of lines are substantially easier to analyze by elimination of lines with high rotational quantum numbers.

It is the principal object of the present invention to provide a method and apparatus adapted to permit accurate quantitative determination of the concentration of a gas in a gas mixture. The method and apparatus should provide for high detection efficiency with good definition and, as a result, little interference. The method and apparatus should be usable for the analysis of a large number of gas mixtures particularly in the control of environmentally noxious compounds.

SUMMARY OF THE INVENTION

This object is achieved with a method and apparatus for the analysis of gaseous compounds, particularly for determining the concentration of a gas in a gas mixture by microwave spectroscopy wherein pulsed microwave radiation is coupled into a frequency tunable resonator disposed in an evacuated receiver into which a gas with air as carrier gas is admitted as a pulsed molecular jet. In this manner air with a given admixture of noxious compounds can be analyzed as samples are taken. As a result of the microwave pulses which are tuned to the frequency of the rotational transitions of the molecules in the gas component be examined, an emission spectrum is generated in the resonator and the emission signals are coupled out from the resonator during the intervals between the microwave pulses and supplied to a signal receiving and analyzing unit in which the concentration of the gas component is determined from the intensity of the emission signal in a process control computer in which preferably the relationship between the concentration of certain gas compounds and their emission spectra is stored in the form of a calibration curve. Also preferably reference measurements are performed during intervals between the molecular jet pulses to provide reference signals from which a corrected signal is developed as the difference between the emission signal and the reference signal.

The method according to the invention provides for faster and more accurate measurements than were obtained by noxious compound measuring methods utilized so far and, as a result of superior definition, interference is practically negligible. Although the gas analysis apparatus disclosed in DE-AS 2442581 operates in accordance with the Stark-effect and utilizes air in combination with gases to be analyzed, it operates with a stationary gas whereas in the arrangement according to the invention the air which is utilized as carrier gas is admitted to the receiver in the form of a pulsed molecular jet stream. It had been firm conviction so far that with such a pulsed molecular stream the use of a gas as carrier gas was an absolute necessity in order to obtain a sufficiently cooled gas mixture during expansion into the evacuated receiver. Such expansion cooling is necessary in order to obtain a sufficiently strong, directly detectable emission signal. However, surprisingly it has now been found that, contrary to the prevailing understanding, a cooling effect can be obtained with air as carrier gas which is sufficient for insuring the required detection efficiency and sensitivity so that particularly the analysis of noxious compounds in the air is facilitated.

The apparatus in accordance with the present invention facilitates utilization of the method outside the laboratories so that concentration of noxious compounds can easily be determined on site. The apparatus according to the invention further has the advantage that it permits rapid switchover from one rotational line to another, that is, from one compound to another.

It is still a further advantage of the invention that only a single source, that is, one microwave synthesizer, is needed for the generation of the polarization microwave on one side and the local microwave on the other. The synthesizer first generates the local microwave whereas the polarization microwave is produced in the single side band mixer provided in accordance with the invention by mixing of the local microwave with a radio frequency wave. The radio frequency wave is generated in a frequency multiplier which is also provided in accordance with the invention and which generates the radio frequency wave from the internal standard frequency of the microwave synthesizer. All functions of this synthesizer can be controlled by a control computer. Utilization of such a microwave synthesizer distinguishes the apparatus according to the invention not only from an arrangement as described in the magazine "Review of Scientific Instruments" referred to before, but also from a so-called MRR (molecular rotational resonance) spectrometer as described in the "Hewlett-Packard Journal", June 1971, pages 2 to 16. The spectrometer described therein, which in any case operates according to a different principle, utilizes as microwave source a so-called Backward Wave Oscillator (BWO) which is stabilized on the basis of a harmonic frequency of a radio frequency synthesizer and which therefore must be newly stabilized with each change of the microwave frequency. Since the microwave synthesizer utilized in the apparatus according to the invention permits a rapid computer controlled frequency change-over and, consequently, rapid change-over from the analysis of one to that of another gas component, the measuring procedure can be highly automated and becomes suitable for use outside the laboratory.

In order to further improve sensitivity and accuracy of the measuring process a number of measuring cycles may be averaged. The possible pulsing frequency depends mainly on the capacity of the available pumping system.

The method and apparatus according to the invention are usable for all gaseous molecules which have suitable rotational lines in the available frequency range of the microwave source. It is furthermore possible, particularly for small, light molecules, to form with a carrier gas, such as nitrogen, association complex compounds, so-called van-der-Waals complexes, which may then be analyzed by rotation spectroscopy. Heavier molecules could be thermally dissociated or fragmented by employing a heated inlet nozzle and they can then be analyzed by way of the fragments.

The method according to the invention accordingly can be utilized in the total area of conventional microwave spectrometry but is not limited thereto. Rather the method can be utilized for a larger number of molecules and molecular complexes in connection with measuring noxious compounds in the air and also for the analysis of process gases.

SHORT DESCRIPTION OF THE DRAWING

The sole FIGURE is a schematic representation of the microwave spectrometer on the basis of which the method and apparatus according to the invention are explained in principle.

DESCRIPTION OF THE PREFERRED EMBODIMENTS

In a receiver 1 there is arranged a microwave resonator of a type known as Fabry-Perot Cavity Resonator which consists of two concave mirrors 2 and 3 arranged opposite one another. In the embodiment shown in the figure, one of the two concave mirrors 2 is firmly mounted in the receiver 1 whereas the second concave mirror 3 is so supported that it is movable along the center axis of the two mirrors 2 and 3, a controllable drive 4 being associated with the mirror 3 for position adjustment thereof. The firmly mounted concave mirror 2 has a bore extending through its center and receiving a supply line 5 which passes through one of the end walls of the essentially cylindrical receiver 1 for feeding in the microwave radiation. At its circumference about in the middle between the two concave mirrors 2 and 3 the receiver is provided with two tubular extensions projecting normal to the longitudinal axis of the cylindrical receiver 1, the tubular extension 6 being provided at its end face with an inlet nozzle 8, and the tubular extension 7 being connected to a two-stage evacuation system including two pumps 9 and 10. The pump 9 which generates the final vacuum is a diffusion pump. A fuel injection nozzle as utilized for gasoline engines is suitable for use as the inlet nozzle 8. The receiver 1 and the system of pumps 9, 10 are combined into a modular unit in the present embodiment.

The components for the generation of the microwave radiation and for the handling and analysis of the measurement signals are contained in a second modular unit. These components include in particular a microwave synthesizer 11 for the generation of microwaves, a directional coupler 12, two frequency multipliers 13 and 14, a single side band mixer 15, two PIN diode switches 16 and 17, a microwave amplifier 18, a circulator 19, two additional mixers 20 and 21, two narrow band amplifiers 22 and 23 and an analog-digital converter 24. There is finally provided a control computer 25 which is in communication with the drive 4, the synthesizer 11, the A/D converter 24 and a control unit 27 by way of bus ducts 26. The control unit 27 is connected to the two PIN diode switches 16 and 17 and to the inlet nozzle 8.

The synthesizer 11 is adapted to produce a microwave radiation of a frequency which in the present embodiment is about by 160 MHz lower than the rotational frequency of the gas molecules whose concentration is to be determined. The directional coupler 12 splits the microwave radiation into two radiation parts, one part being supplied to the single side band mixer 15. Here, the frequency of the incident radiation is mixed with a frequency of 160 MHz and preferably the upper side band generated whose frequency now corresponds to the emission frequency of the gas molecules. The microwave with its frequency so changed is supplied to the PIN diode switch 16. The standard frequency of 160 MHz as well as a frequency of 130 MHz which is needed for signal processing are generated each in the frequency multipliers 13 and 14 respectively by multiplication of the internal standard frequency of 10 MHz of the synthesizer 11.

The first PIN diode switch 16 converts the original continuous microwave radiation to a pulsed radiation with a pulse duration of up to about 2000 Nanoseconds which is amplified in the microwave amplifier 18 and coupled into the microwave resonator 2, 3 by way of the circulator 19. The PIN diode switch 16 is controlled by the control unit 27 which is under control of the process control computer 25.

In the resonator 2, 3, the molecules of the gas to be analyzed are brought into quantum mechanical mixed states which leads to the emission of microwave radiation of a frequency which is characteristic for the molecule. By means of the circulator 19 this emission signal is coupled out from the resonator and transferred into the subsequent receiving arrangement. For this purpose the second PIN diode switch 17 is opened after the end of each microwave pulse under the control of the control unit 27. For the duration of the microwave pulse the PIN diode switch 17 serves as protection for the receiving arrangement. The emission signal is then mixed in the mixer 20 using the second part of the microwave radiation from the directional coupler 12 so as to assume an intermediate frequency of about 160 MHz. After a narrow band amplification of the intermediate frequency in the amplifier 22, the emission signal is mixed again with a frequency of 130 MHz which is obtained from the second frequency multiplier 14. The so generated signal with a frequency of about 30 MHz is again amplified in the amplifier 23 and finally converted in the A/D converter 24 to a digital signal which is supplied to the process control computer 25 for signal value averaging and for further processing, in the present case for Fourier analysis.

The measurement procedure with the apparatus described above is as follows: In order to determine a rotational spectrum a small amount of a given gas mixture whose composition is to be determined is admitted by way of the inlet nozzle 8, into the receiver 1 in which a pressure of less than $10^{-2}$ pascal is maintained. As a result there is formed in the receiver a molecular jet oriented normal to the axis of the microwave resonator 2, 3. At the same time a microwave pulse is coupled into the resonator 2, 3 which has a resonance frequency corresponding to the rotational transition to be observed and which therefore stimulates the compounds to be analyzed to emit radiation of its specific rotational spectrums which is coupled out from the resonator 2, 3 via the supply line 5. Tuning of the resonator 2, 3 to the respective molecular transition frequency is achieved by changing the distance between the two concave mirrors 2 and 3, that is, by changing the axial position of the concave mirror 3 by way of the drive 4 under the control of the process control computer 25. The emission signal is supplied to the receiving and analyzing arrangement.

The emission signal which fades in time, in the present case, is digitized in intervals of 10 to 500 Nanoseconds and is stored in the process control computer. Recording of a measurement takes about 10 to 500 microseconds. For further utilization the received signal is freed from noise if necessary by averaging, and by Fourier transformation the typical rotational frequency is determined. The recorded emission signal is dependent, in a complex manner, on the concentration of the gases, molecular parameters, for example, of the rotational transition, and apparatus parameters. For the development of this complex function in the present case, there is provided for a molecular signal-free recording in the period between two pulses of the molecular jet and, by determination of the difference of the two signals, the influence of the apparatus parameters is eliminated.

If for each of the compounds to be analyzed a calibration curve is recorded and stored in the process control computer 25, the concentration of such compound can be determined by comparison with the calibration curve. For switch-over from one compound to another the process control computer 25 will change the excitation frequency and the distance between the mirrors 2 and 3 for which procedure only a few seconds are needed so that the quantitative composition of a gas mixture can be determined quite rapidly.

LIST OF REFERENCE NUMERALS

1—Receiver
2, 3—Concave mirrors (microwave resonator)
4—Drive
5—Supply line
6, 7—Tubular extensions
8—Inlet nozzle
9, 10—Vacuum pumps
11—Synthesizer
12—Directional coupler
13, 14—Frequency multiplier
15—Single side band mixer
16, 17—PIN diode switches
18—Microwave amplifier
19—Circulator
20, 21—Mixers
22, 23—Amplifiers
24—A/D converter
25—Process control computer
26—Bus duct
27—Control unit

What is claimed is:

1. A method for determining the concentration of compounds in a gas mixture by analysis of the emission spectrum generated by gaseous molecules which are stimulated to rotational transitions by microwave irradiation in a receiver which is evacuated and includes a microwave resonator tunable to the frequency of the rotational transitions to be examined and further a receiving and analyzing unit for processing the signals generated and a computer, said method comprising the steps of admitting air or a gas mixture including compounds to be examined into said receiver as a pulsed molecular jet, supplying to the microwave resonator microwaves of a frequency which about corresponds to the frequency of the rotational transitions to be examined whereby the molecules of said substance generate in the resonator an emission spectrum, coupling the emission spectrum out from the resonator and supplying it to said receiving and analyzing unit, and determining the concentration of said compound from the intensity of its emission signal.

2. A method according to claim 1, wherein the relationship between the concentration of certain gas compounds and the intensity of their emission spectra is, before the actual measurement, determined in the form of a calibration curve which is stored in the computer.

3. A method according to claim 1, wherein the emission spectrum is subjected in said receiving and analyzing unit to a Fourier analysis.

4. A method according to claim 1, wherein there are predetermined intervals between the molecular jet pulses and wherein reference measurements are performed during said intervals to provide a reference signal and the difference between the emission signal and the reference signal is determined to form a corrected emission signal.

5. A method according to claim 4, wherein the pulsing frequency for said pulsed molecular, jet is up to 100 Hz.

6. A method according to claim 4, wherein the duration of the microwave pulses is in the range of 0.10 to about 2000 Nanoseconds.

7. A method according to claim 1, wherein the emission signal measured is digitized at scanning intervals of about 10 to 500 Nanoseconds.

8. A method according to claim 1, wherein the measured emission signal is mixed in at least one frequency mixing step to assume a frequency in the range of 1 to about 50 MHz and this signal is subsequently digitized.

9. An apparatus for examining, and determining the concentration of, compounds in a gas mixture by analysis of the emission spectrum generated by gaseous molecules when stimulated to rotational transitions by microwave irradiation, said apparatus comprising at least one microwave generator including a microwave synthesizer having at least one frequency multiplier and a single side band mixer adapted to generate the microwaves for irradiation of said molecules, a receiver having a microwave resonator disposed therein, said microwave resonator consisting of two spaced concave mirrors arranged opposite one another and supported adjustably for permitting adjustment of their distance from one another, means for admitting said substances to said receiver as pulsed molecular jets, means for coupling the microwave radiation into said resonator in a pulsed manner, including means for controlling the pulse frequency for the microwave radiation and also for the measuring signal path, and means for mixing frequencies in order to obtain a desired frequency, and a receiving and analyzing unit with an amplifier, means for coupling an emission spectrum generated by said molecules under microwave irradiation out from the resonator in said receiver and equipment for the analysis of the emission spectrum signal received from the resonator including means for determining the intensity of the emission signal as an indication of the concentration of a particular compound in the gas mixture.

10. An apparatus according to claim 9, wherein said microwave generator includes a microwave synthesizer, a directional coupler, at least one PIN diode switch and a microwave amplifier connected to the exit of the microwave synthesizer, and providing a path for coupling the microwave radiation into the resonator.

11. An apparatus according to claim 10, wherein a single microwave conduit is provided for coupling the microwave radiation into the resonator and coupling the molecule-generated emission signal out from the resonator at the same mirror.

12. An apparatus according to claim 11, wherein a circulator is provided for coupling the microwave radiation into the resonator and coupling the emission signal out from the resonator.

13. An apparatus according to claim 12, wherein the signal path includes at least one PIN diode switch connected to the exit of the circulator as well as at least one mixer and an amplifier.

14. An apparatus according to claim 13, wherein said directional coupler is connected with a first mixer disposed in the signal path by way of a microwave conductor extending between the two.

15. An apparatus according to claim 14, wherein said signal path includes a second mixer and an amplifier disposed between said first and second mixers.

16. An apparatus according to claim 15, wherein two frequency multipliers are provided, one being connected to said single side band mixer and the other to said second mixer, said frequency multipliers being adapted to be loaded with the internal standard frequency of said microwave synthesizer.

17. An apparatus according to claim 10, wherein said signal path has associated therewith an analog/digital converter and a process control computer connected to the converter.

18. An apparatus according to claim 17, wherein said receiver has an inlet nozzle mounted thereon and a control unit is provided for admission of said molecules so as to provide a pulsed molecular jet stream into said receiver.

19. An apparatus according to claim 18, wherein said control unit is connected to said process control computer.

20. An apparatus according to claim 17, wherein at least one of the concave mirrors of said resonator includes a drive controlled by said process control computer for adjusting the position of said one mirror relative to the other.

* * * * *